United States Patent [19]

Lundquist

[11] Patent Number: 4,468,222

[45] Date of Patent: Aug. 28, 1984

[54] INTRAVENOUS LIQUID PUMPING SYSTEM AND METHOD

[75] Inventor: Ingemar H. Lundquist, Oakland, Calif.

[73] Assignee: Valleylab, Boulder, Colo.

[21] Appl. No.: 99,322

[22] Filed: Dec. 3, 1979

Related U.S. Application Data

[63] Continuation of Ser. No. 868,894, Jan. 12, 1978, abandoned, which is a continuation of Ser. No. 689,115, May 24, 1976, abandoned.

[51] Int. Cl.³ .................... A61M 5/00; F04B 9/08; F04B 35/02
[52] U.S. Cl. .................... 604/153; 417/236; 417/238; 417/360; 417/385; 417/395; 417/560; 417/566; 417/53
[58] Field of Search .............. 92/13.7, 98 R, 101, 92/102; 417/360, 383–389, 395, 236, 238, 454, 560, 566; 128/214 F, DIG. 12

[56] References Cited

U.S. PATENT DOCUMENTS

| | | | |
|---|---|---|---|
| 1,651,964 | 12/1927 | Nelson | 417/395 |
| 1,764,712 | 6/1930 | Brackett et al. | 417/439 X |
| 2,667,184 | 1/1954 | Hailer et al. | 92/98 R |
| 2,980,032 | 4/1961 | Schneider | 417/479 |
| 2,988,001 | 6/1961 | D'Arcey et al. | 417/429 |
| 3,124,214 | 3/1964 | Aselman | 92/13.7 X |
| 3,127,846 | 4/1964 | Kerns | 417/566 X |
| 3,234,943 | 2/1966 | Metz | 417/566 X |
| 3,307,481 | 3/1967 | Castelet | 417/395 X |
| 3,664,770 | 5/1972 | Palmer | 417/383 |
| 3,901,231 | 8/1975 | Olson | 92/13.7 X |
| 3,976,402 | 8/1976 | Lundquist | 417/566 |
| 3,985,133 | 10/1976 | Jenkins et al. | 128/214 F |

FOREIGN PATENT DOCUMENTS

| | | | |
|---|---|---|---|
| 528191 | 5/1954 | Belgium | 417/386 |
| 577326 | 2/1954 | Canada | 417/388 |
| 800805 | 12/1950 | Fed. Rep. of Germany | 417/478 |
| 1287836 | 9/1972 | United Kingdom | 417/477 |

*Primary Examiner*—Edward K. Look
*Attorney, Agent, or Firm*—Flehr, Hohbach, Test, Albritton & Herbert

[57] ABSTRACT

Intravenous Fluid Pumping System having a controller and a pump controlled by the controller. The controller has a sealed chamber with a flexible membrane covering a portion thereof. An incompressible fluid is disposed in the chamber. A piston member is movable in the chamber causing extension and retraction of the membrane as the piston is moved in and out relative to the chamber. A motor is provided for reciprocating the piston. The pump has a pump body with a pumping chamber therein with one portion of the pump body being covered by a flexible membrane in contact with flexible membrane carried by the sealed chamber of the controller. The pump has an inlet adapter connected to the source of fluid. The pump also has an outlet adapter connected to the patient. Inlet and outlet valves are provided in the pump body whereby when the controller is operated to flex the membrane of the sealed chamber of the controller, the diaphram of the pump is operated to cause movement of the valve members to cause fluid to pass from the source through the pump and to the patient under the control of the pump. The controller is also provided with an alarm system whereby positive and negative pressure conditions in the pumping chamber can be sensed.

In the method a piston-like member is used to positively cause displacement of a liquid within a sealed chamber to cause movement of a flexible membrane forming a portion of the sealed chamber. The movement of the flexible membrane causes simultaneous movement of another flexible membrane in intimate contact with the first-named flexible membrane. The movement of the second flexible membrane is used to create a pumping action in a pump having a pumping chamber in which the last-named flexible membrane forms a part of the pumping chamber.

37 Claims, 13 Drawing Figures

Fig_10

Fig_11

Fig_8

Fig_9

INTRAVENOUS LIQUID PUMPING SYSTEM AND METHOD

This is a continuation, of application Ser. No. 868,894 filed Jan. 12, 1978 now abandoned, which is a continuation of Ser. No. 689,115 filed May 24, 1976, now abandoned.

BACKGROUND OF THE INVENTION

Intravenous pumps heretofore have been provided. Attempts have also been made to provide disposable pumps. However, it has been found that such disposable pumps are still relatively expensive and are relatively inaccurate. There is, therefore, a need for a new and improved intravenous pump which is very inexpensive so that it can be thrown away after use. There is also a need for a relatively inexpensive controller for operating the same so that intravenous liquids and the like can be administered with great precision.

SUMMARY OF THE INVENTION AND OBJECTS

The intravenous liquid pumping system and method is adapted to be used with a source of intravenous liquid for supplying such intravenous liquid to a patient. The intravenous liquid pumping system consists of a controller which includes a pump actuator together with a pump. The pump actuator is provided with a sealed chamber. A portion of the chamber is formed by a flexible membrane with the remainder of the chamber being formed with substantially rigid side walls. An incompressible fluid is disposed in the sealed chamber. A piston is mounted for sliding movement in the chamber for movement in and out of the incompressible liquid in the chamber for causing extension and retraction of the flexible membrane as the piston is moved. The controller is provided with means for causing such a movement of the piston in a programmed manner. The pump consists of a pump body having a pumping chamber, a portion of which is covered by a flexible membrane. The pump is provided an inlet which is adapted to be connected to the source of the liquid and an outlet which is adapted to be connected to the patient. Inlet and outlet valve means are provided for controlling the flow of intravenous liquid through the pump chamber. Means is provided for positioning the pump so that the membrane carried by the pump is in intimate contact with the membrane of the pump actuator so that as the piston is moved the membranes of the actuator and the pump will move in unison to create a pumping action in the pump and to cause intravenous liquid to move from the inlet to the outlet in accordance with the displacement of the piston.

In general, it is an object of the present invention to provide an intravenous liquid pumping system and method which includes a controller and a pump of the type in which the pump is disposable and which still can precisely and independent of nominal pressure variations meter intravenous liquid to the patient.

Another object of the invention is to provide a system and method of the above character in which the positive displacement principle is utilized in connection with the operation of the pump.

Another object of the invention is to provide a system and method of the above character in which a pump actuator is utilized having a membrane and in which the pump has a membrane and the membranes move in unison to create a pumping action.

Another object of the invention is to provide a system and method of the above character in which the pump can be used as a flow-through device without disconnecting the pump from the patient.

Another object of the invention is to provide a system and method of the above character in which a controller is utilized having capabilities of sensing underpressure and overpressure conditions in the pumping chamber.

Another object of the invention is to provide a system and method of the above character in which the return stroke is very rapid so as to provide a substantially continuous supply of intravenous liquids to the patient.

Another object of the invention is to provide a system and method of the above character which can be readily utilized by medical personnel.

Another object of the invention is to provide a system and method of the above character in which the displacement can be precisely controlled to thereby control the amount of intravenous liquids dispensed with each stroke.

Another object of the invention is to provide a system of the above character in which the pump is formed of very few parts so that it can be readily fabricated at a low cost.

Additional objects and features of the invention will appear from the following description in which the preferred embodiments are set forth in detail in conjunction with the accompanying drawings.

DESCRIPTION OF THE PREFERRED EMBODIMENT

Figure 1:
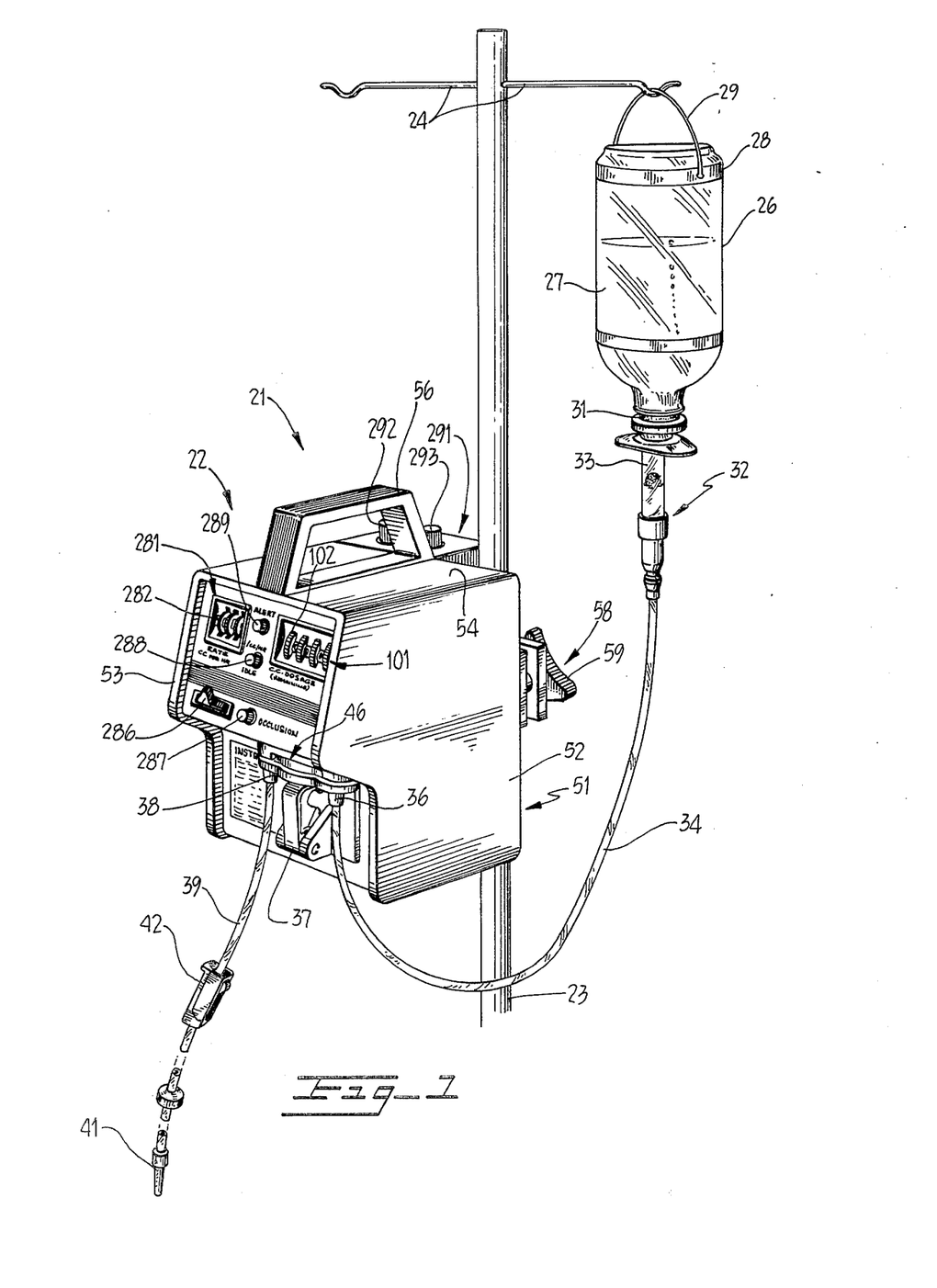
FIG. 1 is an isometric view of a controller and a pump incorporating the present invention mounted upon a conventional stand and being supplied with intravenous liquid from a conventional bottle.

The intravenous liquid pumping system 21 incorporating the present invention is shown in FIG. 1 and consists of a controller 22 which is mounted upon a support stand 23 of a conventional type. The support stand 21 is provided with a pair of outwardly extending support arms 24 which are mounted on the upper end of the support stand 23. A source of intravenous (IV) liquid is provided and is shown in FIG. 1 and is in the form of a conventional IV bottle 26 which contains an IV liquid 27. The IV bottle 26 is provided with a hanger assembly 28 which has a hanger 29 adapted to be secured to the outer end of one of the support arms 24. The IV bottle 26 is provided with a stopper 31 in the neck of the bottle.

A universal drip chamber and spike assembly 32 is inserted into the stopper 31 and extends downwardly therefrom. This universal drip chamber and spike assembly 32 is described in copending application Ser. No. 689,114, filed May 24, 1976 now U.S. Pat. No. 4,055,176. It includes a drip chamber 33 which is connected by a flexible tube 34 to the inlet 36 of an intravenous liquid pump assembly 37. The intravenous liquid pump assembly 37 is provided with an outlet 38 with an outlet tube 39 mounted therein. The outlet tube 39 is connected to a conventional adapter or collar 41 which is adapted to have connected thereto a conventional injection needle (not shown). The injection needle is adapted to be inserted into the vein of a patient so that the IV liquid can be delivered into a vein of the patient. A clamp 42 is mounted on the outlet tube 39 for stopping flow of IV liquid through the tube 39.

The intravenous fluid pump assembly 37 is driven by a pump actuator assembly 46 which is secured to the controller 22 as hereinafter described.

The controller 22 consists of an outer case 51 which is provided with vertical side walls 52 and 53 and a horizontal top wall 54. A carrying handle 56 is mounted on the top wall 54. The outer case 51 is provided with a rear wall (not shown) to which there is secured a clamping assembly 58 which is utilized for securing the controller to the support stand 23. The clamping assembly 58 includes a hand knob 59 for tightening the clamping assembly 58 so that the controller 22 is maintained in a vertical position on this support stand 23.

A framework 61 is mounted within the outer case 51 and consists of a vertical plate 62 which is secured to a front panel 63 by frame nuts 64, which engage upper and lower horizontal portions 63a and 63b of the front panel. The front panel in addition is provided an inclined portion 63c which is inclined downwardly and outwardly at the upper portion of the front panel. It is also provided with a horizontal portion 63d which adjoins the portion 63c and also adjoins the vertical portion 63e. The portion 63e adjoins the lower horizontal portion 63b. The framework 61 includes an L-shaped member 66 which is secured to the vertical frame member 62 by frame nuts assembly 67.

A control mechanism 71 is carried by the framework 61 and includes a drive motor 72 and is of a conventional type, for example, it can be a DC stepper motor, such as one manufactured by the Hurst Mfg. Corp. of Princeton, Ind., Model AS 12 volt DC. The drive motor 72 is mounted upon a gear reducing assembly 73 that is mounted upon spacers 74 and is secured to the vertical plate 62 by screws 76. The gear reducing assembly 73 reduces the speed of the output shaft (not shown) of the drive motor 72 by a predetermined ratio, as for example, 5 to 1. It should be appreciated that, if desired, other ratios, as for example 10 to 1, can be utilized. The principal purpose of the gear reducing assembly 73 is to provide a speed reduction so that the output shaft 77 from the gear reducing assembly can be rotated at a very low rate of speed, as for example, a speed from 1500 revolutions per minute down to almost a standstill.

Two cams, a dosage cam 81 and a piston cam 82, are mounted upon the output shaft 77 and are secured to the shaft 77 by a pin 83 so that both cams 81 and 82 are rotating in unison with the shaft 77. The outer end of the shaft 77 is supported by an L-shaped member 84 which is secured to the vertical plate 62 by screws 86. The L-shaped member 84 carries a bearing 87 which supports the outer end of the shaft 77 (see FIG. 3).

The dosage cam 81 engages a roller 91 rotating upon a pin 92. The pin 92 is mounted in the lower end of a slide member 93 which is mounted for vertical movement on the vertical plate 62 by means of a pair of studs 94 mounted upon the vertical member 62. The studs 94 extend through elongate slots 96 provided in the slide member. A washer 97 is mounted on the outer extremity of each of the studs and is retained in position by a retaining ring 98. The slide member 93 is L-shaped (see FIG. 2) with its longer leg 93a extending in a generally vertical direction and its shorter leg 93b extending in a generally horizontal direction. The shorter leg 93b engages an actuator pin 99 of a predetermining counter assembly 101. The predetermining counter assembly 101 is of a conventional type such as one supplied by Veeder Root. The counter assembly 101 is of a predetermining type and is provided with a plurality of hand wheels dials 102 to permit setting of the desired dosage in cc's. By way of example, the lowest of the hand wheels or dials 102 can be adjusted in increments of 0.2 of a cc with a total range of settings up to 999.8 cc in the counter assembly 101. As can be seen from FIGS. 1 and 2, the dials 102 are accessible from the upper right hand front side of the controller 22. When the counter assembly 101 has been preset to a predetermined number, each revolution of the output shaft 77 will cause the slide member 93 to be raised to substract one increment, as for example, 0.2 cc or 2 milliliters from the counter total.

The L-shaped slide member 93 is provided with a recess 103 in the shorter leg 93b which serves to weaken the leg 93b so that the outer extremity of the same can be adjusted to properly position the same with respect to the actuator pin 99 of the predetermining counter.

The piston cam 82 engages a ball bearing assembly 106 which is mounted upon a stud 107 secured to the lower end of a roller arm 108 through means such as a retaining ring 109. A spacer 111 is provided on the stud 107 to maintain a predetermined spacing between the roller arm 108 and the ball bearing assembly 106. The roller arm 108 is secured by suitable means such as riveting to a sleeve bearing 112 which is rotatably mounted on a large stud 113 carried by the vertical plate 62. The bearing 112 is held in place on the stud 113 by a retaining ring 114 which engages the stud.

A yield arm 116 is provided and has its upper end riveted to a sleeve bearing 117 which is rotatably mounted upon the bearing 112 and thus rotates on an axis which is coincident with the axis of rotation for the roller arm 108. The roller arm 108 and the yield arm 116 are mounted for movement independent of each other.

A cylindrical member 118 is mounted on the yield arm 116 and is normally positioned below one side of the roller arm 108. The yield arm 116 is provided with a tab 119 extending outwardly at right angles therefrom. One end of a spring 121 is secured to the tab 119 and the other end of the spring 121 is secured to a pin 122 mounted on an ear 123 formed as a part of the roller arm 108.

An actuator arm 126 has its upper end secured to an actuator arm bearing 127 by suitable means such as rivets. The sleeve bearing 127 is rotatably mounted upon the stud 113 and is retained thereon by a retaining ring 128. The roller arm 108 is provided with a forwardly extending lobe 129 (see FIG. 2). A spring 131 has one end of the same secured to the lobe 129 and has the other end secured to an ear 132 provided on the actuator arm 126.

A leaf spring switch assembly 133 of a conventional type is secured to an outwardly extending ear 134 provided on the actuator arm 126. The leaf spring switch assembly 133 is provided with two leaves 136 and 137 and a center leaf 138 and which carry contacts 139. The center leaf 137 is provided with an extension 137a which is adapted to be engaged by a cylindrical pin 141 carried by the roller arm 108.

Means is provided for adjusting the stroke of the roller arm and consists of a lever 143 which is pivotally mounted upon a pin 144 secured to the L-shaped member or bracket 84. An eccentric 146 is mounted in the lever 143 and is adapted to be positioned by a screw 147 threaded into the bracket 84 to adjust the angle of the pivot arm on the pivot pin 144. An additional screw 148 is provided for locking the adjustment lever 143 in the desired position. The adjustment lever 143 is provided with a lobe 149 which is adapted to be engaged by the lower extremity of the roller arm 108 and to limit the travel of the lower end of the roller arm in one direction. As hereinafter described, this adjustment makes it possible to determine the accuracy of displacement of the piston.

An 180° shutter 151 is secured to the dosage cam 81, rotates with the dosage cam, and is secured thereto by a screw 152 threaded into a boss 153 provided on the dosage cam. The shutter 151 travels through a slot 154 provided in a housing 156 which carries photoelectric sensing means in the form of a photoelectric cell (not shown) disposed in housing on one side of the slot and a light source (not shown) such as an incandescent lamp mounted in the housing 156 on the other side of the slot 154. Rotation of the shutter 151 will occlude the passage of light to the photoelectric cell during 180° and during the other 180° of travel of the shutter 151 will permit the light rays to pass through into the photoelectric cell. The housing in the 156 is carried by an L-shaped bracket 157 mounted on the vertical plate.

As the piston cam 82 is rotated, the roller arm 108 will have its lower end move back and forth under the control of the piston cam 82 by means of the stud 118 carried by the yield arm 116 to transfer motion to the actuator arm 126. As can be seen, particularly from FIG. 2, the actuator arm 126 is provided with a forwardly extending portion 126a which has an outer rounded end 126b that is adapted to engage the upper end of a piston or plunger 161 of the pump actuator assembly 46.

The pump actuator assembly 46 is mounted in a hole 162 in the horizontal portion 63d of the front panel 63. It consists of a pump receptacle 163 formed of a suitable material such as plastic. The pump receptacle is provided with a flat plate-like member 164 which has its outer extremities secured to the portion 63d of the front panel 63 by screws 165. The plate-like member 164 has a centrally disposed opening 166 formed therein. First and second annular steps 167 and 168 are formed in a plate-like portion and are concentric with the opening 166. A fluid transfer membrane 171 having a circular configuration is disposed within the opening 166 and has an outer stepped annular margin 172 which seats upon the step 167 and is clamped therein by a reservoir forming member 173. The reservoir forming member 173 is bonded to the pump receptacle 163 by suitable means such as ultrasonics so that a liquid-tight seal is formed between the reservoir forming member 173 and the flexible fluid transfer membrane 171.

The upper end of the reservoir forming member 173 is provided with a bore 174 for receiving the lower extremity of the piston plunger 161. Suitable means is provided for forming a liquid-tight seal between the piston or plunger and the reservoir forming member 173 and consists of an O ring 176 (see FIG. 2) which is seated in the upper end of the reservoir forming member 173. A piston guide and cap 177 is mounted on the upper end of the reservoir forming member 173 and is bonded thereto by suitable means such as ultrasonic welding. The piston guide and cap 177 is provided with a cylindrical portion 168 in which the piston 161 is slidably mounted. The piston or plunger 161 is movable between innermost and outermost positions with respect to the reservoir forming member 173. Yieldable spring means is provided for returning the piston or plunger to a retracted or the outermost position and consists of a helical spring 179 which is mounted on the cylindrical portion 178 of the piston guide and cap 177. One end of the spring 179 engages the piston guide and cap 177 whereas the other end engages a ring 181 mounted on the piston and retained thereon by a retaining ring 182. Means is provided for preventing retraction of the piston 161 from the reservoir forming member 173 and consists of an O ring 183 seated in an annular groove 184 provided on the lower extremity of the piston 161. As can be seen, particularly from FIG. 2, the piston 161 is adapted to extend into a seated chamber or reservoir 186 defined by the membrane or diaphragm 171 and by the reservoir forming member 173. This chamber or reservoir 186 is filled with a suitable incompressible liquid 187 through a bore 188 which is normally closed by a screw 189. One liquid 187 found to be satisfactory for this purpose is a #700 silicone fluid supplied by Dow Corning. It is of low viscosity so that it fills all crevices in the chamber 186 to insure displacement of all air from the chamber 186. The silicone liquid is also non-degasible which insures that any displacement by the plunger 161 will be directly represented by a similar displacement of the liquid 187.

The pump receptacle 163 is provided with downwardly extending semi-circular extensions 190 on opposite ends of the plate-like member 164. It is also provided with a pair of bosses 191 which have internally threaded bores 192. Valve engagement screws 193 and 194 are threaded into the bores 192.

Of the pump actuator assembly 46 hereinfore described, all the parts can be formed of relatively inexpensive plastic, with the exception of the membrane 171 which is preferably formed of rubber. The spring 178 and the retaining ring 182 can be formed of metal. The screw 189 can be formed of plastic or metal. The O rings 183 and 176 can be formed of rubber. The piston or plunger 161 can be formed of a suitable plastic material, such as Teflon.

The pump assembly 37 is similarly formed also of principally plastic and is fabricated with as few parts as possible so as to make it relatively inexpensive so that it can be a disposable item to be thrown away after use.

The pump assembly 37 consists basically of three plastic parts which form the pump body 195. The first is a bottom part 196, the second is a middle part 197, and the third is a top part 198. A pump and valve membrane 199 is provided between the middle and top parts. All three of the parts 196, 197, and 198 are ultrasonically bonded together with the pump valve membrane 199 in place. The bottom part 196 is provided with a planar bottom wall 201 with an upstanding lip 202 provided on its outer margin. Inlet and outlet fittings 203 and 204 are formed integral with the bottom wall 201 and have inlet and outlet passages 206 and 207 extending therethrough.

The middle part 197 is also provided with a planar wall 211 which is generally planar to the bottom wall 201. A centrally disposed opening 212 is provided in the wall 211. A depending wall 213 depends from the wall 211 and has a configuration such that it will fit within the upstanding lip 202 provided on the bottom wall 201 of the bottom part 196 so that when the two are ultrasonically welded there is provided a liquid-tight seal between the parts. A centrally disposed pump chamber 216 is defined by the parts 196 and 197.

The middle part 197 is provided with a pair of cylindrical recesses 217 and 218 which extend through the wall 211. A pair of protrusions 219 and 221 are formed on the middle part 197 and are adapted to seat within cylindrical recesses 222 provided in the bottom part 196. A bore 223 is provided in the protrusion 219 and is in communication with the bore 207. It is also in communication with the one side of the cylindrical recess 217. A bore 224 is provided in the protrusion 221 and is in communication with the bore 206. The bore 224 extends upwardly into the center of the recess 213. The middle part 197 is provided with a valve seat 226 which surrounds the bore 224. A similar valve seat 227 is formed in the middle part 197 in the recess 217 and encircles a bore 228 which extends upwardly and centrally into the recess 217. The bore 228 is in communication with a passage 229 which opens into the centrally disposed chamber 216. A passage 231 is provided in the middle part to establish communication between the chamber 216 and the cylindrical recess 218.

The pump and valve membrane 199 includes a pair of members 233 and 234 adapted to engage the valve seats 227 and 226 respectively. The pump and valve membrane 199 is formed of a suitable material such as an elastomer. Each of the valve members consists of an inverted dish-shaped portion 236 and is carried by a stem 237. The upper ends of each of the stems 237 are formed integral with a circular disc 238. The outer margin of each of the discs 238 is enlarged at 239 to provide a configuration similar to that of an O ring.

In addition, the pump and valve membrane 199 is provided with a centrally disposes circular membrane or a diaphragm 241 which is adapted to seat over an upwardly extending lip 247 that surrounds the centrally disposed opening 212. In addition, the pump and valve membrane 199 is provided with an enlarged portion at 243 concentric with the diaphragm 241 to provide a conformation in cross section similar to an O ring.

The pump and valve membrane 199 is clamped into position in the middle part by the top part 198 to establish a liquid-tight seal between the chamber 216 and the recesses 217 and 218 by clamping together the O ring portions found at 239 and 243. The top part 198 also consists of a flat or planar wall 246 which is parallel to the wall 211 and the wall 201. It is provided with a centrally disposed opening 247 through which the diaphragm 241 can extend. As can be seen, the upper surface of the diaphragm 241 is flush with the upper surface of the wall 246. In addition, the wall 246 is provided with two additional smaller openings 248 and 249 disposed on opposite sides of the opening 247 which are adapted to receive the lower extremities of the valve engaging screws 193 and 194 to permit adjustment of the valve members 233 and 234 as hereinafter described.

It can be seen that the pump assembly 37 is constructed in such a manner so that it can be readily inserted into the semi-circular extensions 189 of the pump receptacle 163 and so that the screws 193 and 194 can extend through the holes 248 and 249 to engage the discs 238 carrying the valve members 233 and 234. It can also be seen that the diaphragm 241 is brought into intimate contact with the fluid transfer membrane 171 for a purpose hereinafter described and that a tight seal is established between the outer margins of the same by the clamping action of the annular lip 242 on the pump 37 and another annular lip 250 on the reservoir forming member 173 overlying the lip 242.

Figure 8:
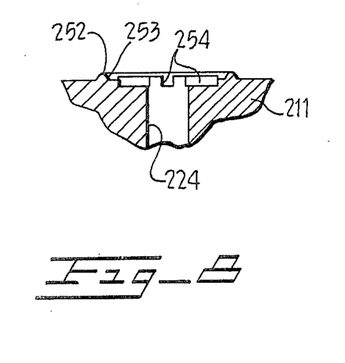
FIG. 8 is a cross-sectional view of a portion of the pump and showing particularly the construction of the valve seat utilized therein.
Figure 9:
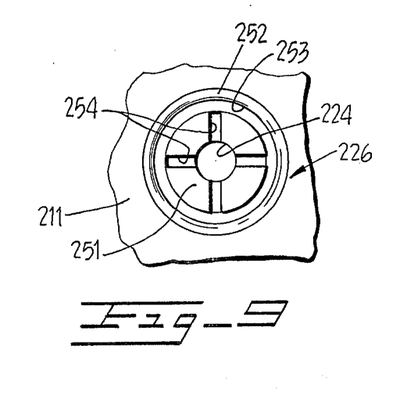
FIG. 9 is a plan view of the portion of the valve seat shown in FIG. 8.

The valve seats 226 and 227 are each provided with a cylindrical raised portion 251 (see FIGS. 8 and 9) which surrounds the bore 226 with respect to the valve seat 226. A raised annular rim 252 is provided as a part of the valve seat and surrounds the raised cylindrical portion 251 but is spaced therefrom to provide an annular recess 253. As can be seen from FIG. 8, the height of the rim 253 is slightly greater than the height of the raised cylindrical portion 251. A plurality of radical channels or passages 254 are provided in the raised cylindrical portion 251 and extend from the central bore 224 to the annular recess 253. As shown in FIG. 9, these channels form an X on the top surface of the raised cylindrical portion 251. The configuration of the valve seats 226 and 227 and the valve members 233 and 234 is such that they provide excellent valve seating capabilities for both negative and positive pressures. In addition, they require less squeezing pressure to achieve a good seal. The channels 254 provided in the raised cylindrical portion 251 make it possible for fluid to pass into the recess 253 to cause opening of the mushroom-shaped or dish-shaped portions 236 of the valve member even though there is a higher pressure on the stem 237 of the valve member. Therefore, it can be seen that the opening and closing of the valve members 233 and 234 are determined primarily by the other extremities or flap portions of the dish-shaped or mushroom type valve members 236 rather than on the pressure applied to the stems of the valve members. This makes the valve members less sensitive to the adjustment provided by the valve screws 193 and 194.

Figure 2:
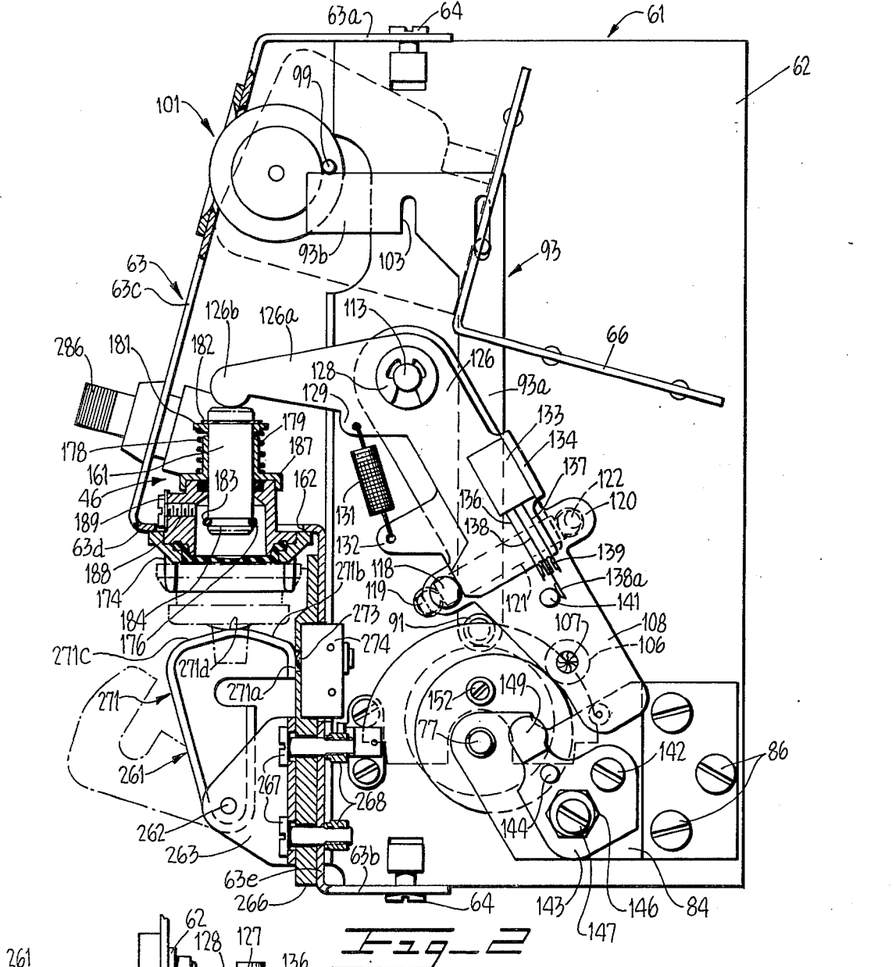
FIG. 2 is a cross-sectional view of the controller shown in FIG. 1.

Means is provided for clamping the pump assembly 37 within the receptacle 163 and consists of a clamping member 261 which is movable from a pump engaging position as shown in solid lines in FIG. 2 and an out-of-the-way position out of engagement with the pump as shown by broken lines in FIG. 2. The clamping member 261 is pivotally mounted upon a pin 262 carried by a U-shaped bracket 263. The bracket 263 is mounted upon a plate 266 formed of a suitable material such as plastic. The bracket 263 and the plate 266 are secured to the front panel 63 by screws 267 threaded into nuts 268. The clamping member 261 has a generally L-shaped configuration in side elevation and is provided with an upper camming surface 271. The camming surface 271 has a generally vertical portion 271a which is adapted to engage the plate 266. It is also provided with a forwardly and downwardly inclined surface portion 271b and a downwardly and rearwardedly inclined portion 271c. The apex of the camming surface 271 can be found at 271d. It can be seen that the length of the surfaces 271b and 271c is such that the highest portion 271d of the clamping member will be moved past the center of the pump assembly 37 as shown in particularly FIG. 2 when the pump assembly 37 is in place. In other words, the clamping member 261 is friction-locked in an over-center position. The clamping member is movable from a position in which it locks the pump assembly 37 into the pump receptacle 163 and an out-of-the-way position, which, as shown in broken lines in FIG. 2, permits removal of the pump assembly 37 from the pump receptacle 163.

When the clamping member 261 is in a pump-retaining position, the front surface 271a engages one end of an operating lever 273 of a microswitch 274 and holds the switch in an open position. The microswitch 274 is mounted in an opening 276 provided in the frame member 62. The microswitch 274 is connected into the electronic circuitry which is utilized for driving the stepping motor 72.

A rate-setting digital control counter 281 of the conventional type is mounted in the upper left-hand portion of the inclined front panel portion 63c as viewed from the front. The counter 281 is provided with a plurality of dials 282 which can be utilized for presetting the rate of operation of the stepping motor. The counter can be calibrated in cc's per hour and by way of example this rate capacity can be from 1 to 600 cc's per hour in 1 cc increments.

An on-off switch 286 is also mounted on the front panel 63 and controls the power to the motor 72 and the electronic circuitry provided within the controller. The electronic circuitry is of a conventional type utilized for supplying energy to the stepping motor to cause it to step in a predetermined rate in accordance with the setting on the rate-setting counter 281. Three lights 287, 288 and 298 are provided on the front panel 63. the light 287 is identified as an "occlusion light". This light is turned on when there is an overpressure condition which occurs when the spring 121 is stretched sufficiently to permit the yield arm 116 to move relative to the roller arm 108 to permit closing of the contacts carried by the leaves 137 and 138 of the switch 133. The light 288 is an "idle light" and is turned on when all the fluid has been delivered as has been set by the predetermined dosage counter 101. As soon as this occurs, the electronics is switched to a keep-open needle rate which may range from 1 to 15 cc's per hour.

The light 289 can be identified as an "alert light" and indicates a negative pressure condition or some other failure mode. For example, if the clamping member 261 is out of engagement with the lever arm 273, the switch 274 will be closed to energize the alert light 289. A negative pressure condition is sensed and when the leaves 138 and 136 have their contacts brought together under the force of the spring 121 to establish a closed circuit for energizing the light 289.

In order to ensure emergency power and also to make it possible to operate the pumping system independent of a source of A/C power, a battery and charging circuit module 291 is mounted on the rear of the case 51 on the upper left-hand corner of the same as shown in FIG. 1. The battery and charging circuit module are provided with a power cord (not shown) which can be connected into a conventional 110 volt A/C outlet so as to provide charging current to the batteries at the same time power is being supplied to the pumping system. The module 291 is provided with two lights 292 and 293 with the light 292 indicating a battery in use or charging situation and with light 293 indicating a low battery condition.

Operation and use of the intravenous fluid pumping system will now be briefly described as follows. Let it be assumed that a pump set has been provided which consists of a pump assembly 37 with an outlet tube 39 connected to a valve fitting 38 and a tube 34 connected to the inlet fitting 36. In addition, let it be assumed that the inlet tube 34 is connected to a universal drip chamber and spike assembly 32 described in U.S. copending application Ser. No. 689,114 filed May 24, 1976 now Pat. No. 4,055,176. Assuming that the pump is to be filled with an intravenous liquid, the roller clamp 42 is closed on the tube 39. The spike of the spike assembly 32 is inserted into the stopper 31 of the bottle. The pump 37 is held in such a manner so that the outlet fitting 38 is above the inlet. The clamp 42 is then loosened to permit liquid to flow into the pump forcing the air ahead of it. Thus, the liquid will pass through the passage 207 provided in the fitting 39. Also it will pass up through the passage 224 and will cause opening of the valve member 234 to permit liquid to flow into the recess 218 and then into the passage 231 into the pump chamber 216. The liquid will then pass into the passage 229 through the bore 228 to the valve member 233 to move the valve member 233 away from the valve seat 227 to permit liquid to enter the recess 217 and then to pass through the bore 223 and the bore 206 out through the outlet fitting 38. Liquid is permitted to continue to flow until liquid passes out through the adapter collar 41 and the needle connected thereto to indicate that all air has been removed from the pump and from the tubing connected to the pump. As soon as this occurs, the clamp 42 is moved to a closed position. The pressure of the liquid will cause bowing outwardly of the diaphragm 241 so that it has a shape of a portion of a sphere.

The valves, when the pump 37 is not mounted in the pump actuating assembly 46, are out of engagement with the valve seats so that the pump is in reality a flow-through device so that it can be readily filled in the manner herein before described or used as a drip set.

After the pump 37 has been filled, it is inserted into the pump receptacle 163 and clamped into place by moving the clamping member 261 from the broken line position shown in FIG. 2 to the solid line position shown in FIG. 1 so that the cam surface 271 engages the pump and moves it upwardly into firm engagement with the pump actuator assembly 46. The clamping member is moved past center to hold the clamp and the pump in position and so that the clamp engages the operating lever 273 of the switch 274.

As pointed out previously, the diaphragm 241 of the pump 37 is bulged outwardly which ensures that, when the pump 37 is placed in the pump receptacle, the diaphragm or membrane 241 first will engage the diaphragm or member 271 in the center and then as the pump 37 is pressed upwardly by the clamping member 261, the air between the membranes 241 and 271 will be forced outwardly from the center to make a perfect contact between the two membranes 241 and 271 with no air between the same. In addition, a seal is formed between the outer margins of the two membranes 241 and 271 by the lips 242 and 250 so that they in fact act in unison like a single membrane.

At the same time that the two membranes 241 and 271 are being brought into contact with each other, the valve screws 193 and 194 extend through the openings 248 and 249 provided in the top part 198 of the pump 37 to engage the elastic discs 238 immediately overlying the stems 237 of the valve members 233 and 234. The valve screws 193 and 194 have been adjusted so that they will bias the valve members 233 and 234 into a normally closed position with respect to the valve seats 226 and 227.

As soon as the disposable pump has been put in place, the contrller 22 can be adjusted and placed in operation. By way of example, the dosage counter can be set so as to deliver a predetermined dosage to the patient, as for example, 200 cc's by adjusting the appropriate dials 102. After the dosage has been determined, the rate of delivery can be set on the rate-setting counter 281. By way of example, assuming that 200 cc's of fluid are to be delivered to the patient for the anticipated dosage, the rate can be set at 100 cc's per hours so that the patient will receive the 200 cc dosage withing two hours. The rate is set by adjusting the dials 282. The switch 286 can then be turned on to place the controller in operation to cause operation of the pump as hereinafter described to cause fluid to be supplied to the needle connected to the adapter 41. The controller 22 can be momentarily turned off by the actuation of the switch 286. The needle can then be inserted into the patient's vein in an appropriate manner and the switch 286 switched to the on position.

As soon as the switch 286 is turned to the on position, power is supplied to the electronics (not shown) which causes signals to be supplied to the stepping motor 72 in accordance with the rate set on the rate counter 281 so that the output shaft 77 is rotated at a predetermined speed in digital steps.

As pointed out previously, this rotation of the shaft 77 causes rotation of the dosage cam 81 and the piston cam 82. The rotation of the dosage cam causes raising of the slide member 92 to cause movement of the actuator pin 99 to deduct one increment, as for example 0.2 of a cc from the dosage counter 101 for each revolution of the dosage cam 81.

Figure 10:
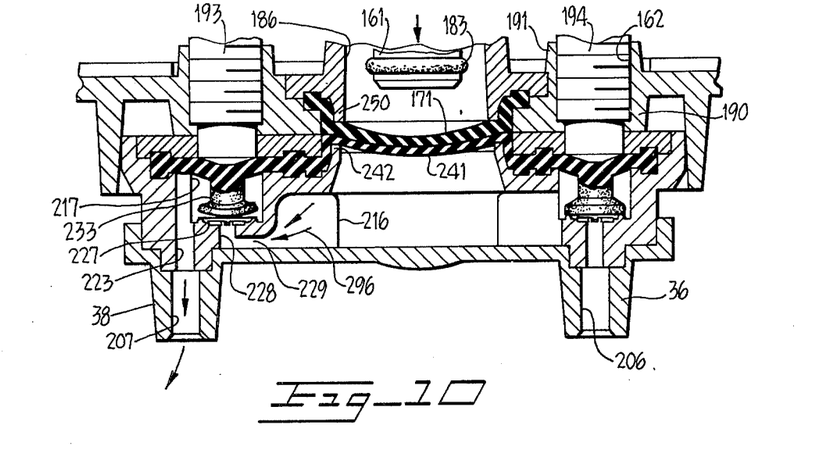
FIG. 10 is a cross-sectional view of the pump actuator and the pump showing operation of the pump during the downward or downstroke movement of the piston and the pump actuator.

At the same time, the piston cam 82 is rotated and causes movement of the free end of the roller arm 108 as the ball bearing assembly 106, carried by the roller arm 108, engages the piston cam 82. This motion of the roller arm 108 is transferred by the stud 122 carried thereby to the spring 121 and thence to the ear 119 connected to the yield arm 116 so that under normal circumstances the yield arm moves with the roller arm. The spring 113 connecting the roller arm to the actuator arm 126 also causes the actuator arm to yieldably move with the yield arm 116 and with the roller arm 108 so that upon each revolution of the piston cam 82 the piston 161 is depressed downwardly against the force of the spring 178. As the piston 161 is moved downwardly into the reservoir 186, the liquid 187 will be forced out of the way or displaced to cause a downward deflection of the membranes 171 and 241 as shown in FIG. 10. This downward deflection of the membranes 171 and 241 will cause displacement of liquid in the pump chamber 216. The displaced liquid will be forced through the passage 229 as indicated by the arrows 296 and then upwardly through the bore 229 to raise the valve member 233 out of engagement with the valve seat 227 to permit the liquid to pass into the recess 217 and thence downwardly through the bore 223 and down the bore 207 provided in the outlet fitting 38 and into the outlet tube 39 to the patient. As hereinbefore described, the stroke of the piston 161 is adjusted so that a predetermined amount of liquid is displaced from the pump upon each stroke, as for example 0.2 of a cc.

As hereinbefore pointed out, the electronics utilized in the controller is such that it is under the control of the rate counter 281 so that the stepping motor 272 is driven at a speed so that the required dosage is delivered within a predetermined period of time. This downstroke of the piston 161 represents 180° rotation of the shutter 151 which subtends an angle of 180°. During this period of time, the photoelectric cell is occluded. As soon as the downstroke has been completed, the photoelectric cell is exposed to the light from the light source because the shutter has moved to an out-of-the-way position. As soon as this occurs, the electronic circuitry causes rapid stepping of the motor 72 so that the output shaft is rapidly rotated through 180° in a relatively short period of time. This return stroke time is kept as low as possible so that as much time as possible is available for delivering a continuous flow of the intravenous liquid to the patient. The return stroke time is constant for all dosage rates. The downstroke, on the other hand, is directly under the control of the rate counter 281. The piston 161 is moved upwardly on its return stroke by the spring 179. This spring also serves to keep the ball bearing roller 106 carried by the roller arm 108 in engagement with the piston cam 82.

Figure 11:
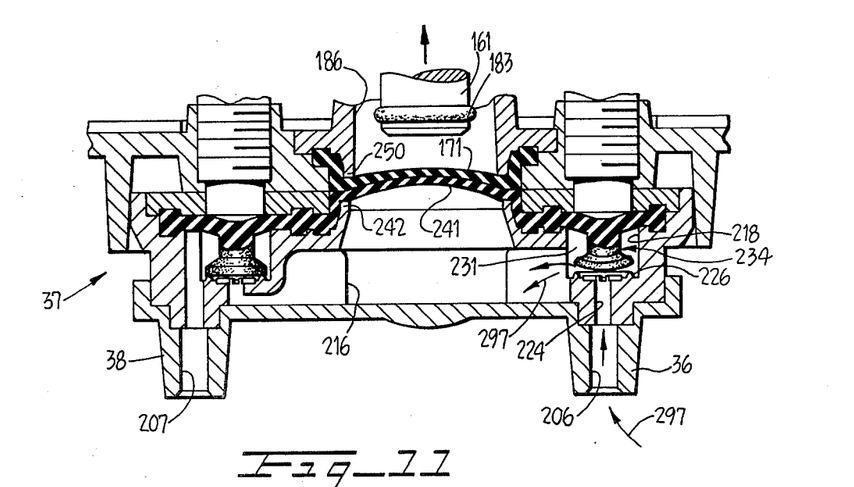
FIG. 11 is a cross-sectional view similar to FIG. 10 but showing the operation of the pump during the upward or upstroke movement of the piston.

The operation of the pump during the downstroke of the plunger 161 is shown in FIG. 10. The operation of the pump 37 during the upstroke (return) stroke of the plunger 161 is shown in FIG. 11. As shown therein, as soon as the piston 161 starts on its return stroke, the flexible membranes 171 and 241 are flexed upwardly. As the piston 161 is withdrawn it reduces the displacement of liquid 187 in the chamber 186 which is accommodated by inwardly flexing of the membrane 171 as shown in FIG. 11. A similar decrease in pressures is created in the chamber 216. Membrane 241 follows the membrane 171 which causes the outlet valve member 233 to move to a closed position with respect to the valve seat 227. It also causes the outer margins of the inlet valve member 234 to be flexed upwardly out of engagement with the seat 226 under the force of the intravenous liquid supplied through the tube 34 to the inlet fitting 36. The liquid then passes through the bore 206 through the bore 224 and thence past the valve seat 226 and into the cylindrical recess 218 through the passage 231 and into the pump chamber 216 as indicated by the arrows 297. This additional intravenous liquid which is brought into the pump chamber during the intake or return stroke of the piston 161 is dispensed by the pump 37 to the outlet fitting 38 during the next downward stroke of the piston 161.

Thus, it can be seen as the controller 22 is operating, upon each downward stroke of the piston 161, a single count representing 0.2 of a cc will be deducted from the dosage counter 101. In this way it is possible for a nurse, who is supervising the operation, to watch the movement of the mechanical counter 101 to ascertain whether fluid is being delivered to the patient. This procedure continues until the entire dosage has been delivered to the patient at which time the counter 101 turns to the number 999.8 which indicates to the electronics that the complete dosage has been supplied to the patient. This causes the electronics to energize the idle light 288 by which means the electronics is automatically switched to operate the stepping motor at an idle rate which as heretofore described may be between 1 cc per hour to 15 cc's per hour or any other desired idle rate. In addition, this signal can be utilized to cause the energization of an audible alarm. The nurse upon hearing the alarm can turn off the alarm and leave the controller 22 operating at the slow rate which a keep-open needle rate so that the pump set can thereafter, if desired, be used to dispense additional intravenous liquids to the patient at a later time.

In the event there is a vacuum condition created within the pump 37, as for example can be caused by an empty bottle 27, the spring 178 will have insufficient force to return the plunger 161. The piston cam 82, however, will continue to move and the roller arm 108 will follow the same and will cause the pin 141 carried thereby to move out of engagement with the leaf spring portion 138a to permit it to move downwardly to engage the contact carried by the leaf 136 to close a circuit to operate an alert alarm by energizing the light 289 and also, if desired, by energizing an audible alarm. Means is provided in the electronic circuitry so that once the alert circuitry is energized, it will be latched electronically so that the alert alarm will not go off when the pin 141 again is moved into engagement with the leaf spring portion 138a during cyclic rotation of the piston cam 82.

As soon as the alarm is heard by the nurse, the nurse can readily remedy the situation by placing a new IV bottle on the spike assembly 32. As soon as this has been accomplished the drip chamber can be filled as described in copending U.S. application Ser. No. 689,114 filed May 24, 1976 now Pat. No. 4,055,176. The vacuum condition in the pump will be alleviated and the spring 178 will have sufficient force to return the piston 161 so that the leaf spring portion 138a will return to its normal position and the alert alarm system will be denergized when the on-off power switch 286 is turned "off" and then "on".

If an overpressure condition occurs, as for example, by the nurse accidentally leaving the clamp 42 on the tube on the distal end of the pump 37, an overpressure condition will be created in the pump, which means an excessive force will be required to move the piston 161 downwardly. As soon as this occurs, the yield spring 121 will yield to change the relationship between the yield arm 116 and the roller arm 108 and also the actuator arm 126 so that the pin 141 carried by roller arm is moved upwardly relatively to the switch 133 so that a contact closure is established with respect to the leaf 137 to establish a closed circuit for energizing the occlusion light 287 so that the nurse as soon as she hears the alarm can remedy the situation. The arrangement is such that other overpressure conditions can be sensed such as those created by a clot in the needle or by the patient lying on the tube and the like. The strength of the spring 121 determines when an overpressure condition is sensed. As can be appreciated, this can be readily adjusted so that an alarm is created at any predetermined range of pressures, as for example, 10-15 pounds per square inch. Thus, it can be seen that with such a mechanism for driving the piston 161, dangerous overpressure conditions cannot be created which would be dangerous to the equipment or to the patient.

With the construction disclosed, it is possible to limit the stroke of the piston 161 to precisely determine how much fluid is dispensed during each stroke of the piston. The upstroke or the return normally would be limited by the bottom position of the piston cam. However, in the present construction, the upstroke is limited by the position of the lobe 149 provided on the lever 143. By adjusting the position of this lever 143, as heretofore described, the length of the stroke for the piston 161 can be adjusted to thereby precisely determine the amount of fluid which will be pumped by the pump during each stroke of the piston.

In the event it is not desired to positively control the flow of the intravenous liquid to the patient by a positive displacement pump, the pump 37 can be removed from the pump receptacle 163 by moving the clamp 261 to the out-of-the-way position. As soon as the pump is moved away from the pump actuating assembly 46, the valve members 233 and 234 move out of engagement with the valve seats 226 and 227 so that the pump in effect is a flowthrough device. Thereafter the flow of intravenous liquid to the patient can be controlled through the universal drip chamber and spike assembly 32 or any other suitable means desired. If it is again desired to utilize the positive displacement pump, it is merely necessary to place the pump in the pump receptacle 163 in the manner hereinbefore described to positively force intravenous liquid into the veins of the patient. Thus, it can be seen that the pump 37 can be utilized as a positive displacement pump for supplying fluid or as a flow-through device without the necessity of disconnecting the intravenous set from the patient.

It is apparent that the intravenous pumping system hereinbefore described has many features and advantages. One of the principle features is that the pump 37 is formed of a very few parts all of which are formed of plastic except for the single rubber part which forms the diaphragm or membrane 241 and the valve members 233 and 234. This means that the parts of the pump can be readily fabricated and assembled. This also makes it possible to make the pump relatively inexpensively so that it can be a throw-away item after it has been used by the patient. The intravenous liquid supplied to the patient as it moves through the pump 37 is completely isolated because the membrane 241 serves as a germ barrier.

The more expensive parts, which are normally associated with the pump, are disposed in the pump actuator assembly 46, as for example, the movable piston and the like. As hereinbefore explained, the pump actuator assembly 46 forms a permanent part of the controller. Even though the piston 161 is separated from the pump chamber 261 by the two membranes 241 and 171, there is no loss of accuracy in the pump because the two membranes 241 and 171 are in intimate contact with each other and precisely follow each other in unison with the movement of the piston 161 so that there is dispensed from the pump chamber 216 the exact amount of fluid which is displaced by the piston 161 in its own chamber 186.

The controller is also advantageous in that it is relatively simple and still provides great precision in the metering of the fluid and control of the total dosage. Also it provides alarms for negative and positive pressure conditions created in the pump without creating degassing conditions with respect to the liquids utilized.

Figure 5:
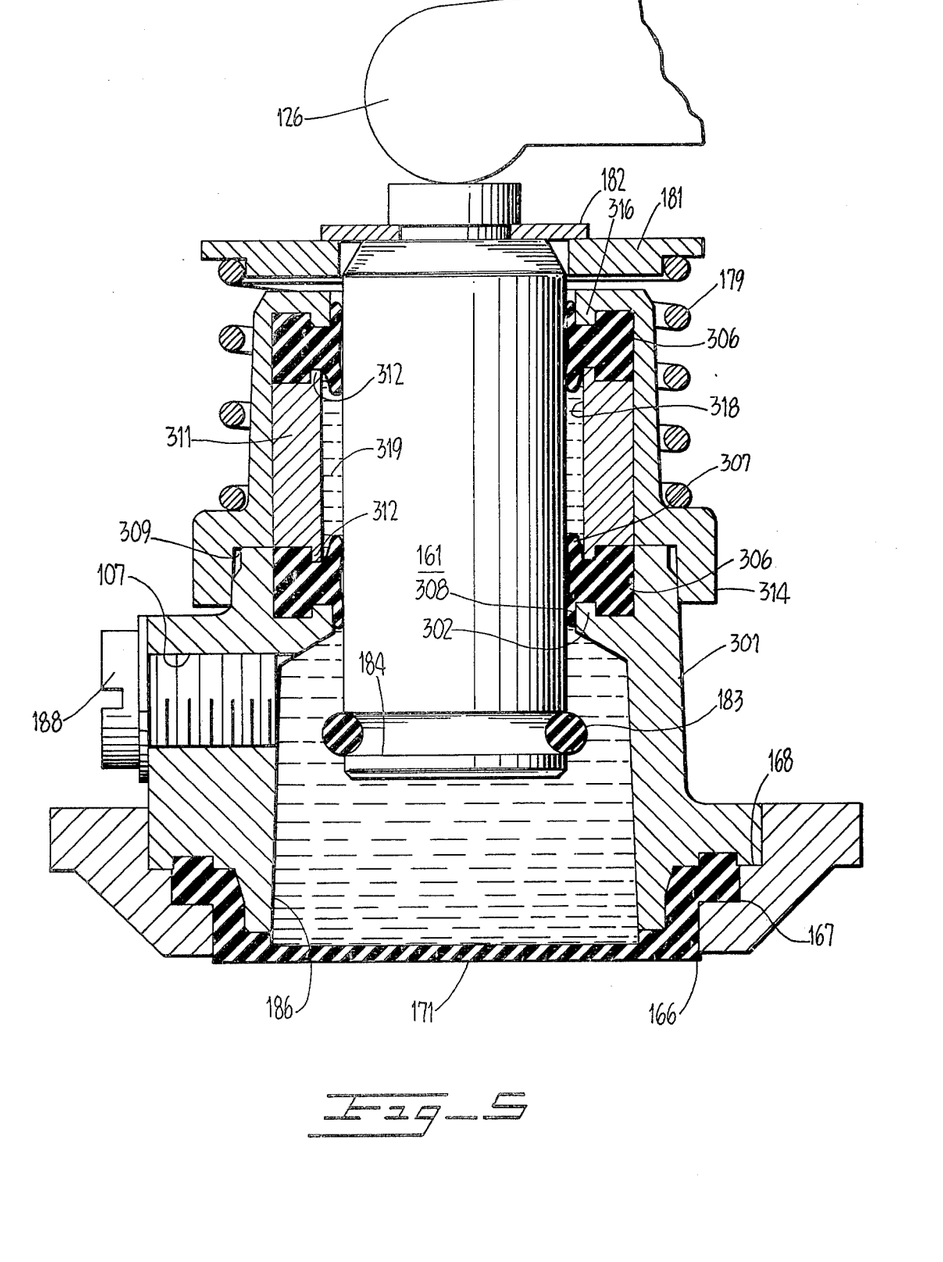
FIG. 5 is a cross-sectional view of another embodiment of the pump actuator utilized in the controller shown in FIG. 2.
Figure 6:
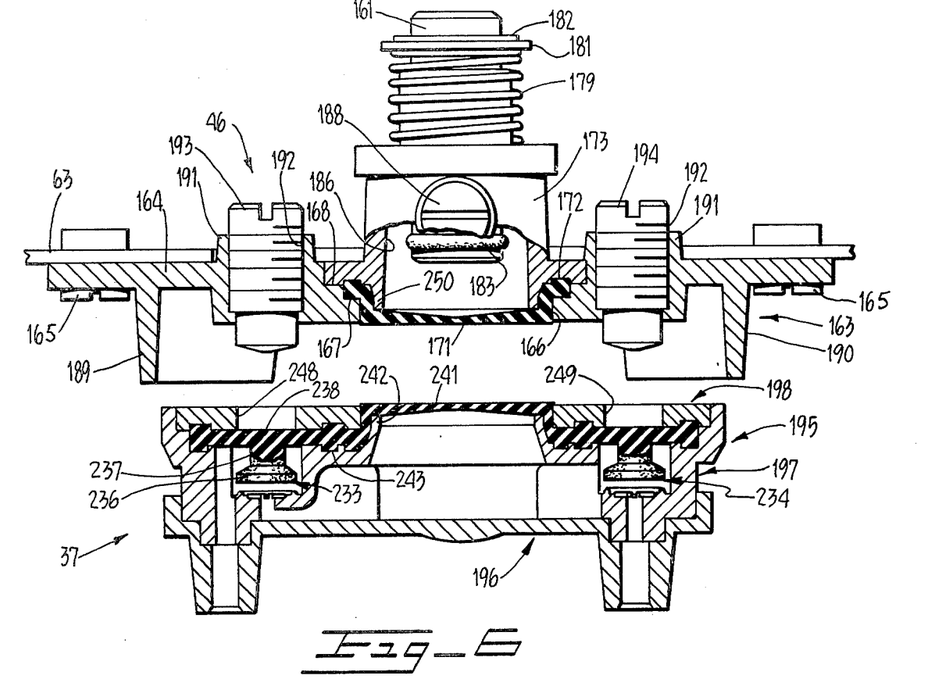
FIG. 6 is a cross-sectional view of the pump actuator and the pump in spaced apart or separated conditions.
Figure 7:
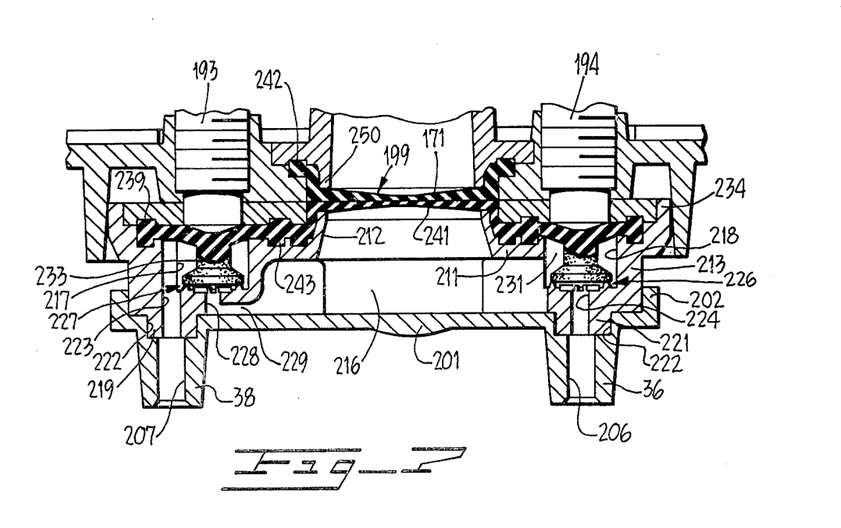
FIG. 7 is a cross-sectional view of a portion of the pump actuator and the pump fastened together for a pumping operation.

Another embodiment of the pump actuator assembly is shown in FIG. 5. Many of the portions of the same are identical to the parts hereinbefore described. However, a revised reservoir-forming member 301 is provided in place of the reservoir-forming member 173. It differs in that its upper extremity is provided with an upwardly extending outwardly spaced inner lip 302 which is adapted to carry one side of an annular lip-type sealing member or ring 306. The sealing member 306 is provided with annular lip-like portions 307 and 308 which are adapted to engage the side wall of the piston 161 to establish sealing engagement therewith. As will be noted, the liplike portions 307 and 308 are slightly curved so that there is provided a slight recess 309 between the extremities of the same.

A ring 311 surrounds the piston 161 and engages the sealing member 306. It is provided with downwardly extending lips and upwardly extending lips 312 which engage the sealing member 306 hereinbefore described. In addition, the upper lips 312 engage another upper sealing member 306 identical to that hereinbefore described. A cylindrical cap 313 is fitted over the sealing rings 306 and over the inner ring 311. It is provided with an outwardly and downwardly extending flange 314 which seats over the top of the reservoir-forming member 301. It is also provided with a downwardly extending lip 316 which engages the upper sealing member 306. The spring 179 identical to that hereinbefore described with the previous embodiment and has one end engaging the flanged portion 314 and has the other end engaging the ring 181. An annular space 318 is formed between the piston 161 and the inner surface of the ring 311. This annular space 318 is filled with a suitable liquid 319 such as silicone so as to establish a liquid and airtight seal between the piston 161 and the cylindrical cap 313. Thus, it can be seen that the liquid 319 in conjunction with the two sealing members 306 form a germ barrier as well as a liquid and airtight seal for the piston 161 so that no air will be introduced into the chamber 186. This is important and it assures that the fluid in the chamber 186 will remain substantially incompressible so that precise metering can take place in accordance with the displacement provided by the piston 161.

Figures 3, 12, 13:
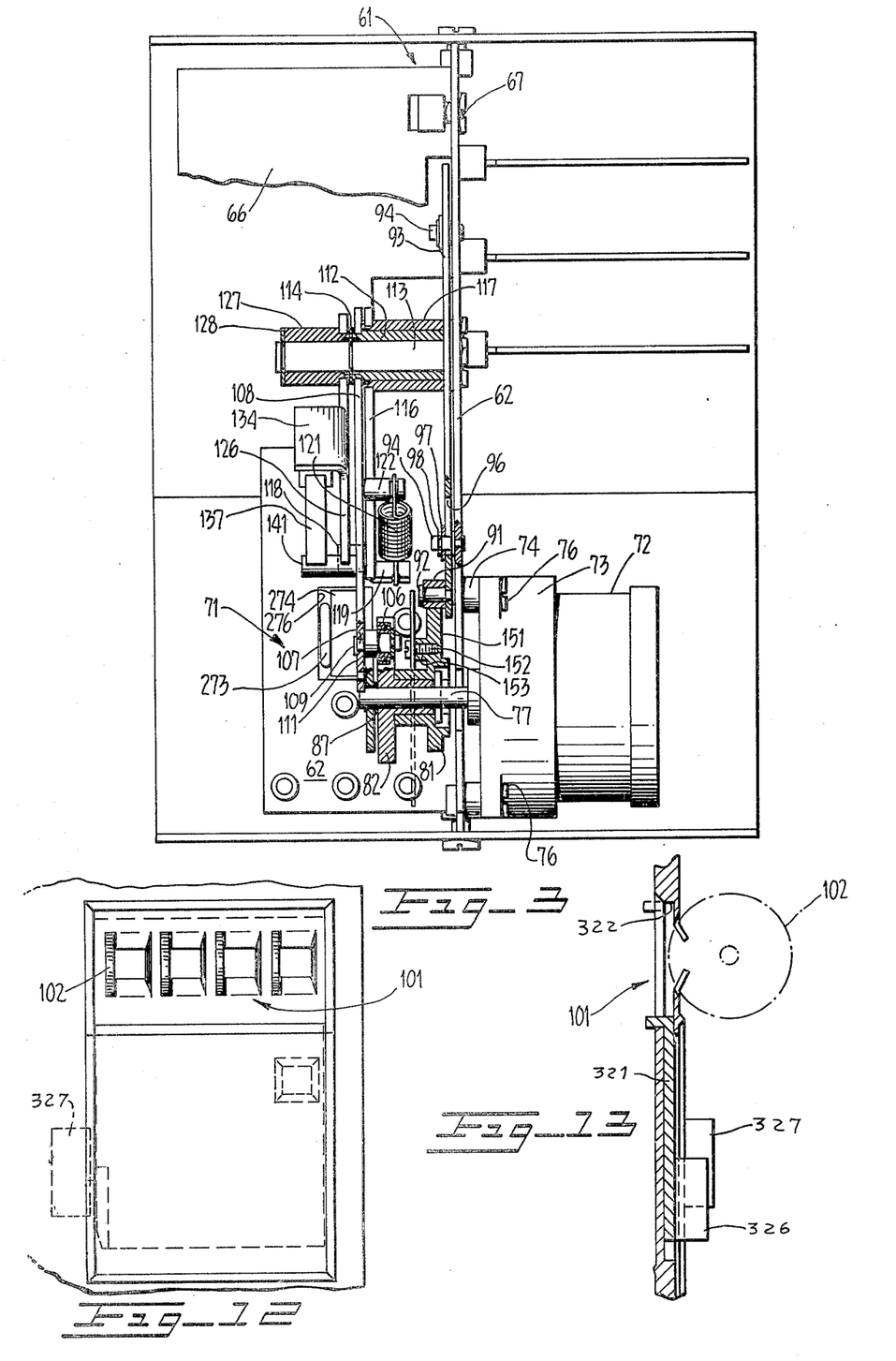
FIG. 3 is a rear elevational view, partially in cross-section, of the controller shown in FIG. 2.
FIG. 12 is a front elevational view of another embodiment of the controller.
FIG. 13 is a cross sectional view of a portion of the controller shown in FIG. 12.
Figure 4:
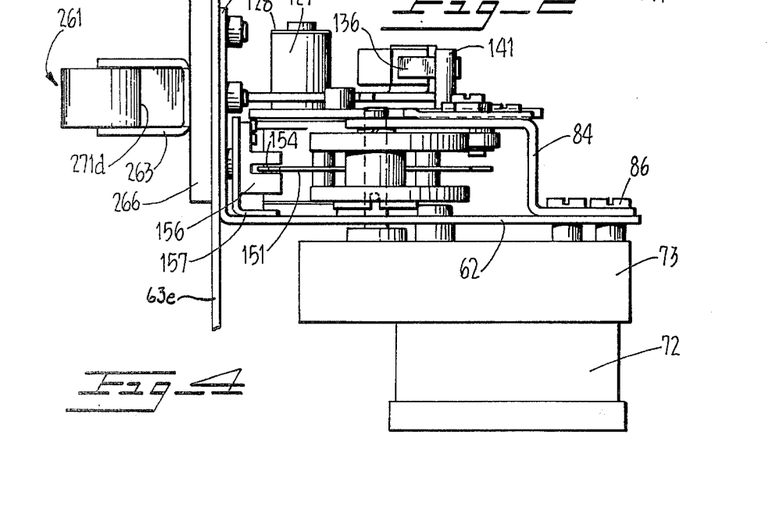
FIG. 4 is a cross-sectional view taken along the line 4—4 of FIG. 2.

Another embodiment of the controllers is shown in FIGS. 12 and 13 in which the predetermining counter assembly 101 having dials 102 has associated therewith a slidable cover 321. The cover 321 is slidably mounted in the front panel 63 for movement between a closed position where it covers an opening 322 as shown in broken lines in FIG. 13 and an open position as shown in solid lines in FIG. 13 where the counter assembly 101 is visible.

The cover 321 can be provided with a suitable legend such as "volume counter and keep open needle rate not in use". To accomplish this function described on the cover 321, the cover 321 is provided with a cam member 326 which is is adapted to operate a Microswitch 327 when the cover is raised to deactivate the keep open needle rate function of the controller.

What is claimed is:

1. In an intravenous liquid pumping system for use with a source of intravenous liquid to be supplied to a patient, a controller, a disposable pump for use with the controller and normally disposed of after a one-time use and clamping means for securing said disposable pump to the controller for easy insertion and removal of the disposable pump, the controller having a controller body forming a chamber with first and second openings in communication therewith, a plunger mounted in said first opening for movement into and out of the chamber between innermost and outermost positions, a flexible membrane carried solely by the controller body to seal said chamber so it is liquid tight, a constant quantity of liquid filling said sealed chamber whereby as said plunger is moved into and out of the liquid the membrane will be moved between extended and retracted positions and motive means for moving said plunger, said disposable pump having a rigid pump body with a pump chamber therein, said pump body having an opening therein in communication with said pump chamber, a flexible membrane carried solely by said pump body, and covering said opening in said pump body, said membrane carried by the pump body being exposed to the atmosphere when it is free of the controller, said pump body having outlet and inlet ports formed therein in communication with the pump chamber, outlet valve means for controlling liquid flow from the pump chamber through the outlet port, inlet valve means for controlling liquid flow into the pump chamber through the inlet port, each valve means including a valve seat and a valve member movable either to an inoperative position spaced from the seat or an operative position in cooperative relationship with the seat, means for biasing each of said valve members to its operative position when the pump is secured to the controller by the clamping means, means adapted to connect the inlet port to the source of liquid and means adapted to connect the outlet port to the patient, said clamping means for securing the disposable pump to the controller including means for positioning the pump so that the flexible membrane carried thereby is in intimate contact with the flexible membrane of the sealed chamber of the controller whereby as the plunger is moved, intravenous liquid is forced through said pump by conjoint movement of said membranes.

2. In an intravenous liquid pumping system for use with a source of intravenous liquid to be supplied to a patient, a controller and a pump for use in the controller, the controller having a sealed chamber with a portion thereof being covered by a flexible membrane, a plunger mounted for movement into and out of the sealed chamber, a liquid filling said sealed chamber whereby as said plunger is moved into and out of the liquid the membrane will be moved between extended and retracted positions, motive means for moving said plunger, said pump having a pump body with a pump chamber therein, a portion of the pump chamber being covered by a flexible membrane, said pump body having outlet and inlet ports in communication with the pump chamber, outlet and inlet valve means for controlling the flow of liquid through the outlet and inlet ports, means adapted to connect the outlet port to the patient and means for positioning the pump so that the flexible-membrane carried thereby is in intimate contact with the flexible membrane of the sealed chamber of the controller whereby as the plunger is moved, intravenous liquid is forced through said pump by conjoint movement of said membranes, said outlet and inlet valve means in said pump including an outlet valve seat formed in the body and surrounding the outlet port, an inlet valve seat formed in the body and surrounding the inlet port, a flexible outlet valve member adapted to engage the outlet valve seat, a flexible inlet valve member adapted to engage the inlet valve seat, said controller including biasing means for biasing the outlet valve member and the inlet valve member into closed positions.

3. A system as in claim 2 wherein said biasing means in the controller includes adjustable screws threaded into the controller and adapted to engage the outlet and inlet valve members.

4. A system as in claim 1 wherein said clamping means for securing said disposable pump to said controller includes manually releasable clamping means for retaining said pump in engagement with the controller when said pump is in use.

5. In an intravenous liquid pumping system for use with a source of intravenous liquid to be supplied to a patient, a controller and a pump for use in the controller, the controller having a sealed chamber with a portion thereof being covered by a flexible membrane, a plunger mounted for movement into and out of the sealed chamber, a liquid filling said sealed chamber whereby as said plunger is moved into and out of the liquid the membrane will be moved between extended and retracted positions, motive means for moving said plunger, said pump having a pump body with a pump chamber therein, a portion of the pump chamber being covered by a flexible membrane, said pump body having outlet and inlet ports in communication with the pump chamber, outlet and inlet valve means for controlling the flow of liquid through the outlet and inlet ports, means adapted to connect the outlet port to the patient and means for positioning the pump so that the flexible-membrane carried thereby is in intimate contact with the flexible membrane of the sealed chamber of the controller whereby as the plunger is moved, intravenous liquid is forced through said pump by conjoint movement of said membranes, said motive means for moving said plunger including a motor having an output shaft, dosage and piston cams driven by said output shaft, a settable predetermining dosage counter, lever means actuated by said dosage cam and for operating said predetermining dosage counter and lever means engaging said piston cam and engaging said plunger for causing movement of said plunger in accordance with the rotation of said cam.

6. A system as in claim 5 wherein said lever means engaging said piston cam includes a pivotally mounted roller arm engaging said piston cam, a pivotally mounted yield arm, a pivotally mounted actuator arm engaging said plunger and being coupled to said yield arm whereby upon movement of said yield arm said actuator arm is operated to cause movement of said plunger.

7. A system as in claim 6 wherein said controller includes switch means and means for mounting said switch means on one of said arms of said lever means engaging said piston cam whereby movement of said yield arm relative to said roller arm causes a contact closure in said switch means to energize an alarm.

8. A system as in claim 7 wherein said switch means is mounted on said actuator arm together with a pin carried by the roller arm for operating the switch means, said switch means including contacts for making a contact closure when overpressure and underpressure conditions are encountered by the plunger.

9. A system as in claim 6 wherein said controller includes means for controlling the length of stroke of said plunger.

10. A system as in claim 9 wherein said means for controlling length of stroke of said plunger includes means for engaging the roller arm for limiting upward movement of the plunger.

11. A system as in claim 1 wherein said controller includes a settable dosage rate control for controlling the rate of operation of said motive means.

12. A system as in claim 1 wherein said controller includes means for causing rapid operation of the motive means during the up stroke of the plunger so as to maximize the time which can be utilized during the down stroke of the plunger for delivery of intravenous liquid to the patient.

13. In a controller for use in an intravenous liquid pumping system of the type including a removable pump assembly having a rigid pump body having an opening therein and a flexible membrane carried by the pump body and closing said opening, said controller comprising a rigid controller body having a chamber formed therein with first and second openings, a plunger mounted in said first opening for movement into and out of the chamber between innermost and outermost positions, means for yieldably urging said plunger towards its outermost position, a flexible membrane carried solely by the controller body and covering said second opening to form said chamber in combination with said plunger into a liquid-tight chamber, a constant quantity of liquid filling said chamber whereby as said plunger is moved into and out of the liquid the membrane carried by the controller will be extended and retracted and motive means for causing movement of said plunger, said membrane carried by the controller having its outer surface exposed to the atmosphere and adapted to be engaged by the membrane carried by the pump body to cause simultaneous movement of the membrane carried by the pump body and the membrane of the controller as the membrane of the controller is moved by the movement of the plunger of the controller.

14. A controller as in claim 13 wherein said means for yieldably urging said plunger towards its outermost position includes yieldable spring means mounted on said controller body engaging said plunger for urging said plunger towards an extreme upstroke position.

15. A controller as in claim 14 wherein said motive means includes a drive motor having an output shaft, a plunger cam driven by said shaft, lever arm means engaging said plunger cam and engaging said plunger for causing downstroke movement of said plunger against the force of the yieldable spring means.

16. A controller for use in intravenous liquid pumping systems, a controller with a chamber therein, a portion of the chamber being covered by a flexible membrane, a plunger mounted for movement into and out of the chamber between innermost and outermost positions, a liquid filling said chamber whereby as said plunger is moved into and out of the liquid the membrane will be extended and retracted and motive means for causing movement of said plunger, said motive means for causing movement of said plunger including yieldable spring means mounted on said controller body engaging said plunger for urging said plunger towards an extreme upstroke position, said motive means also including a drive motor having an output shaft, a plunger cam driven by said shaft, lever means engaging plunger cam and engaging said plunger for causing a downstroke movement of said plunger against the force of the yieldable spring means, said lever arm means including first, second and third levers with the first lever engaging the plunger cam and the third lever engaging the plunger and spring means for connecting said second lever to said first and third levers.

17. A controller as in claim 16 together with switch means carried by one of said first, second and third levers whereby upon relative movement of said levers with respect to each other, said switch means will be operated to initiate an alarm.

18. A controller as in claim 17 wherein said switch means is capable of ascertaining whether said plunger encounters an overpressure or underpressure condition.

19. A controller as in claim 16 together with means for limiting the stroke of said plunger, said means for limiting stroke of said plunger including a stop member adapted to be engaged by the first lever arm and means for adjustably positioning the stop member.

20. In a pump for use with a source of liquid and a patient and with a controller of the type having a rigid controller body with a chamber formed therein having first and second openings extending into the chamber, a plunger mounted in the first opening for movement into and out of the chamber between innermost and outermost positions, a flexible membrane carried solely by the controller body and covering said second opening in the controller body and in combination with said plunger sealing said chamber so that said chamber is liquid tight, a liquid filling said sealed chamber whereby as the plunger is moved into and out of the liquid, the membrane will be moved between extended and retracted positions and motive means for moving said plunger, said pump comprising solely a rigid pump body forming a pump chamber and an opening in communication with said pump chamber, a flexible membrane exposed to the atmosphere carried solely by said pump body and closing said opening in said pump body, said pump body having outlet and inlet ports in communication with said pump chamber with the outlet port being adapted to be connected to the patient and the inlet port being adapted to be connected to the source of liquid, outlet valve means for controlling liquid flow from the pump chamber through the outlet port, inlet valve means for controlling the flow of liquid through the inlet port into the pump chamber, each valve means including a valve seat and a valve member movable either to an inoperative position spaced from the seat or an operative position in cooperation with the seat, and means for biasing each of said valve members to its inoperative position when the pump is separated from the controller, said pump being capable of being positioned in proximity to said controller so that the flexible membrane of the pump is in intimate contact with the membrane of the controller whereby when the plunger is moved, the membrane on the pump will be moved to cause operation of the inlet and outlet valve means and a pumping action with liquid being supplied to the patient from the source.

21. In a pump for use with a source of liquid and a patient and with a controller of the type having a rigid controller body with a chamber formed therein having first and second openings extending into the chamber, a plunger mounted in the first opening for movement into and out of the chamber between innermost and outermost positions a flexible membrane carried solely by the controller body and covering said second opening in the controller body and in combination with said plunger sealing said chamber so that said chamber is liquid tight, a liquid filling said sealed chamber whereby as the plunger is moved into and out of the liquid, the membrane will be moved between extended and retracted positions and motive means for moving said plunger, said pump comprising solely a rigid pump body forming a pump chamber and an opening in communication with said pump chamber a flexible membrane exposed to the atmosphere carried solely by said pump body and closing said opening in said pump body, said pump body having outlet and inlet ports in communication with said pump chamber with the outlet port being adapted to be connected to the patient and the inlet port being adapted to be connected to the source of liquid and outlet and inlet valve means movable between open and closed positions for controlling flow of liquid through the outlet and inlet ports so that when said outlet and inlet valve means are in closed positions the chamber in the body is liquid tight and when the outlet and inlet valve means are in open positions liquid can pass from the inlet port through the chamber in the pump body and out the outlet port, said pump being capable of being positioned in proximity to said controller so that the flexible membrane of the pump is in intimate contact with the membrane of the controller whereby when the plunger is moved, the membrane on the pump will be moved to cause a pumping action with liquid being supplied to the patient from the source, said outlet and inlet valve means including an inlet valve seat formed in the body and an outlet valve seat formed in the body and flexible inlet and outlet valve means adapted to be moved into engagement with the inlet and outlet valve seats, said inlet and outlet valve means including means for biasing them into normally open positions.

22. In a pump for use with the source of liquid and a patient and a controller of the type having a sealed chamber with a portion thereof being formed by a flexible membrane, a plunger mounted for movement into and out of the sealed chamber between innermost and outermost positions, a liquid filling said sealed chamber whereby as the plunger is moved into and out of the liquid the membrane will be moved between extended and retracted positions, motive means for moving said plunger and valve biasing means, said pump comprising a pump body having a chamber formed therein, a portion of said pump chamber being formed by a flexible membrane, said pump body having outlet and inlet ports in communication with the pump chamber, the outlet port being adapted to be connected to the patient and the inlet port being adapted to be connected to the source of liquid and outlet and inlet valve means for controlling the flow of liquid through the outlet and inlet ports said pump being capable of being positioned in proximity to said controller so that the flexible membrane of the pump is in intimate contact with the membrane of the controller whereby when the plunger is moved, the membrane on the pump will be moved to cause a pump action with liquid being supplied to the patient from the source, said outlet and inlet valve means including an inlet valve seat formed in the body and an outlet valve seat formed in the body and flexible inlet and outlet valve members adapted to be moved into engagement with the inlet and outlet valve seats, said pump being adapted to be positioned with respect to said controller so that said valve biasing means biases said inlet and outlet valves towards the inlet and outlet valve seats.

23. A pump as in claim 21 wherein said inlet and outlet valve means includes flexible valve members and wherein said valve members and said membrane of said pump are formed integral with each other.

24. In a pump for use with the source of liquid and a patient and a controller of the type having a sealed chamber with a portion thereof being formed by a flexible membrane, a plunger mounted for movement into and out of the sealed chamber between innermost and outermost positions, a liquid filling said sealed chamber whereby as the plunger is moved into and out of the liquid the membrane will be moved between extended and retracted positions, motive means for moving said plunger and valve biasing means, said pump comprising a pump body having a chamber formed therein, a portion of said pump chamber being formed by a flexible membrane, said pump body having outlet ports in communication with the pump chamber, the outlet port being adapted to be connectd to the patient and the inlet port being adapted to be connected to the source of liquid and outlet and inlet valve means for controlling the flow of liquid through the outlet and inlet ports, said pump being capable of being positioned in proximity to said controller so that the flexible membrane of the pump is in intimate contact with the membrane of the controller whereby when the plunger is moved, the membrane on the pump will be moved to cause a pumping action with liquid being supplied to the patient from the source, said outlet and inlet valve means including an inlet valve seat formed in the body and an outlet valve seat formed in the body and flexible inlet and outlet valve members adapted to be moved into engagement with the inlet and outlet valve seat, said flexible inlet and outlet valve members including a mushroom-shaped valve, a valve stem formed integral with the valve and a disc-like member formed integral with the valve stem.

25. A pump as in claim 24 wherein said pump body is provided with an opening through which the flexible member is exposed and wherein said pump body is provided with openings overlying the disc-like members.

26. A controller as in claim 20 together with sealing means for establishing a seal between the controller body and the plunger.

27. A controller as in claim 26 wherein said means for establishing a seal between the controller body and the plunger includes spaced annular sealing means engaging the plunger and a liquid disposed between the spaced annular sealing means and the controller body for filling the space between the annular sealing means so that no air is present in said space.

28. In a method for causing pumping of an intravenous liquid from a source of liquid to a patient by the use of a controller having a controller body with a chamber formed therein and first and second openings in communication with the chamber, a piston-like member mounted in the first opening for movement between first and second positions, a flexible membrane carried solely by the controller body and closing said second opening to seal said chamber so that it is liquid tight, and a constant volume of liquid disposed in said chamber and by the use of a pump having a pump body with a pump chamber formed therein and an opening in communication with the pump chamber, a flexible membrane carried solely by said pump body and closing said opening in said pump body, said pump body having inlet and outlet ports formed therein, and inlet and outlet valves carried in the pump body for controlling the flow of liquid through the inlet and outlet ports, the method comprising connecting the inlet to the source of liquid, filling the pump chamber with liquid from the source so that there are no air bubbles in the pump chamber, placing the pump body in contact with the controller so that the membrane carried by the pump body is in intimate contact with the membrane carried by the controller, connecting the outlet to the patient, causing movement of the piston-like member to cause displacement of the liquid in the chamber and thereby cause movement of the flexible membranes carried by the controller and the pump and to thereby cause liquid from the source to be pumped through the pump chamber to the patient, disconnecting the outlet from the patient and the inlet from the source, separating the pump from the controller and normally disposing of the pump after only one use.

29. A method as in claim 28 wherein the displacement of the membrane of the pump is directly proportional to the movement of the piston-like member.

30. A separate and independent pump assembly for use with a source of liquid and a patient and consisting of a rigid pump body having a chamber formed therein adapted to receive said liquid, said body having an opening formed therein which is in communication with the chamber, a substantially planar flexible membrane having an exterior surface exposed to the atmosphere covering said opening in said pump body, said pump body being formed with inlet and outlet ports spaced from said opening in communication with said chamber, said inlet port being adapted to be connected to the source of liquid, said outlet port being adapted to be connected to the patient, inlet valve means for controlling the flow of liquid through the inlet into said chamber, and outlet valve means for controlling the flow of liquid from the chamber through the outlet, each valve means including a valve seat and a valve member movable to either an inoperative position spaced from the seat or to an operative position in cooperative relationship with the seat, means for yieldably urging each of the valve members to its inoperative position to permit liquid to flow through the pump independent of movement of the membrane, said membrane being movable between extended and retracted positions to cause operation of said inlet and outlet valve means whereby liquid is caused to flow into the chamber through the inlet port and out of the chamber through the outlet port.

31. A pump assembly as in claim 30 wherein said flexible membrane and said inlet and outlet valve means are formed integrally of a rubber-like material.

32. A separate and independent pump assembly for use with a source of liquid and a patient and consisting of a pump body having a chamber formed therein adapted to receive said liquid, a portion of said chamber being formed by a flexible membrane having an exterior surface exposed to the atmosphere, said pump body being formed with inlet and outlet ports in communication with said chamber, said inlet port being adapted to be connected to the source of liquid, said outlet port being adapted to be connected to the patient and inlet and outlet valve means disposed in the inlet and outlet ports for controlling the flow of liquid through the inlet and outlet ports, said membrane being movable between extended and retracted positions to cause liquid to flow into the chamber through the inlet port and out of the chamber through the outlet port, said inlet and outlet valve means including means for biasing the same into normally open positions to permit liquid to readily flow from the inlet port through the chamber and through the outlet port.

33. A pump assembly as in claim 32 for use with external valve biasing means and wherein said pump body is formed to receive said external valve biasing means for biasing said inlet and outlet valve means from their normally open positions to closed positions.

34. In a pumping apparatus, a body having a chamber for containing liquid, the body having an inlet for supplying liquid to the chamber and an outlet for delivering the liquid to a patient, valve means for controlling flow through the inlet into the chamber, valve means for controlling flow from the chamber through the outlet, each valve means including a valve seat and a valve member movable to either an inoperative position spaced from the seat or to an operating position in cooperative relationship with the seat, a receptacle against which the body is adapted to be clamped, means for biasing each of said valve members to its inoperative position when the body is separated from the receptacle and means for moving each of said valve members to its operating position relative to its corresponding seat when the body is clamped to the receptacle.

35. A pumping apparatus as in claim 34 in which two spaced diaphragms of resilient material are disposed in one wall of the body, each of said valve members being attached to a corresponding diaphragm, said diaphragms when the body is separated from the receptable serving to bias said valve members to the inoperative positions of the same, and in which said means for moving each of said valve members to its operating position includes members for flexing said diaphragms in a direction toward the interior of the chamber when the body is clamped to said receptacle, whereby said valve members are moved to operating positions of the same.

36. Apparatus as in claim 34 together with a controller fixed with respect to the receptacle, a pumping diaphragm in one wall of the body and adapted to be flexed to vary the volumetric capacity of the chamber, and means for operatively coupling the controller to said diaphragm when the body is clamped to the receptacle, the controller when operating serving to recurrently flex the diaphragm to effect pumping action.

37. A pumping apparatus as in claim 36 in which the controller includes a body forming a closed liquid containing chamber, a plunger extending into the body of the controller and adapted to be reciprocated, and a flexible diaphragm of resilient material forming one wall of the chamber of the controller, said diaphragm of the controller being pressed into interface contact with the diaphragm of the first named body when the first named body is clamped against the receptacle, thereby providing the aforesaid coupling means.

* * * * *